(12) United States Patent
Uskokovic

(10) Patent No.: US 7,491,711 B2
(45) Date of Patent: *Feb. 17, 2009

(54) METHODS OF TREATMENT USING 3-DESOXY VITAMIN D3 ANALOGS

(75) Inventor: Milan Radoje Uskokovic, Upper Montclair, NJ (US)

(73) Assignee: Roche Palo Alto LLC, Palo Alto, CA (US)

(*) Notice: Subject to any disclaimer, the term of this patent is extended or adjusted under 35 U.S.C. 154(b) by 271 days.

This patent is subject to a terminal disclaimer.

(21) Appl. No.: 10/246,359

(22) Filed: Sep. 18, 2002

(65) Prior Publication Data

US 2003/0130241 A1 Jul. 10, 2003

Related U.S. Application Data

(60) Provisional application No. 60/323,870, filed on Sep. 21, 2001.

(51) Int. Cl.
*A01N 45/00* (2006.01)
*C07C 401/00* (2006.01)

(52) U.S. Cl. ...................... 514/167; 552/653

(58) Field of Classification Search ................. 514/167, 514/168; 552/653
See application file for complete search history.

(56) References Cited

U.S. PATENT DOCUMENTS

| | | | | |
|---|---|---|---|---|
| 4,225,596 | A * | 9/1980 | DeLuca | 514/167 |
| 4,264,512 | A * | 4/1981 | Okamura et al. | 552/541 |
| 5,484,782 | A * | 1/1996 | DeLuca et al. | 514/167 |
| 5,585,368 | A | 12/1996 | Steinmeyer et al. | |
| 6,372,731 | B1 * | 4/2002 | Kirsch et al. | 514/167 |
| 6,559,138 | B1 * | 5/2003 | Uskokovic | 514/167 |

OTHER PUBLICATIONS

Qaqish et al. "Bone disorders associated with the human immunodeficiency virus" 2004, Pharmacotherapy, 24(10), 1331-46.*
Zamboni et al. "Association of osteopetrosis and vitamin D-resistant rickets" 1977, Helv. Paediatr. Acta., 32(4-5), 363-8.*
Okamura et al. "Vitamin D and its analogs" 1975, Biochemical and Biophysical Research Communications, 65(1), 24-30.*
Koike, et al., "20-Cyclopropyl-cholecalciferol Vitamin D3 Analogs," *Anticancer Research*, (1999) pp. 1689-1697, vol. 19:(3A).
Uskokovic, et al., "The 16-ene Analogs of 1,25-Dihydroxycholecalciferol. Synthesis and Biological Activity," (1991) pp. 139-145 from *Proceedings of the Eighth Workshop on Vitamin D* Paris, France.
A. Inzerillo et al., "Skeletal Fragility in the Elderly" in *Geriatric Medicine* 4th Ed., C. K. Cassel, Ed. in Chief, Springer, NY, 2003, p. 621-649.
P. D. Jardine & D. Thompson "Anti-Osteoporosis Agents" in *Annual Reports in Medicinal Chemistry* Chapter 22,1996 31:211.

A. Gray & I. R. Reid "Emerging and potential therapies for osteroposis" *Expert Opin. Investig. Drugs* 2005 14(3):265-278 at 269.
J. Aerssens et al., "Effect of 1α-Vitamin $D_3$ on Bone Strength and Composition in Growing Rats with and without corticosteroid therapy" *Calcif. Tissue Int.* 1994 55:443-450.
S. Pelarge et al., "Cellular and Molecular Events Associated with the Bone-Protecting Activity of the Noncalcemic Vitamin D Analog Ro-26-9228 in Osteopenic Rats" *Endocrinol* 143(5): 1625.
A. I. Castillo et al. "Characterization of Vitamin D Receptor Ligands with Cell-Specific and Dissociated Activity" *Mol. Endocrinol* 2006 20(12):3093-914.
V. N. Shankar et al. "Metabolism of a 20-methyl substituted series of Vitamin D analogs by cultured human cells: apparent reduction of 23-hydroxylation of the side chain by the 20-methyl group" *Biochem. Pharmacol.* 2001 61:893-902.
R. Bouillon et al. "Structure-Function Relationships in the Vitamin D Endocrine System" *Endocrin Rev.* 1994-5 16(2):200-256.
A. S. Lee et al., "3-Deoxy-3-thia-1α,25-dihydroxyvitamin $D_3$ and Its 1β Epimer: Synthesis and Biological Evaluation" *J. Org. Chem.* 1992 57(14):3846-3854.
R. Marcus, "Agents Affecting Calcification and Bone Turnover". In *Goodman & Gilman's The Pharmacological Basis of Therapeutics*, 10th Ed.; J. G. Hardman & L. E. Limbird, Editors-in-Chief; McGraw-Hill, New York, 2001, p. 1725.

(Continued)

*Primary Examiner*—Sreeni Padmanabhan
*Assistant Examiner*—Kara R McMillian
(74) *Attorney, Agent, or Firm*—Brian L. Buckwalter

(57) ABSTRACT

The present invention provides a method for treating osteoporosis, hyperparathyroidism or an autoimmune disease in a patient by administering to the patient a 3-desoxy vitamin $D_3$ analog of the formula:

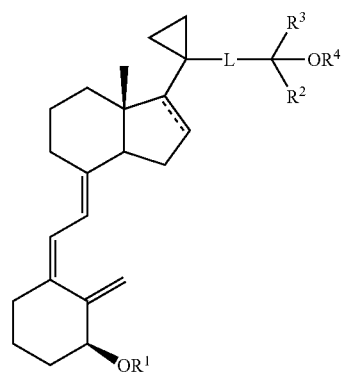

a prodrug or a salt thereof, where the dotted line, $R^1$, $R^2$, $R^3$, $R^4$ and L are those defined herein. The present invention also provides methods for producing 3-desoxy vitamin $D_3$ analog of Formula I.

10 Claims, No Drawings

OTHER PUBLICATIONS

National Osteoporosis Foundation. Physician's guide to prevention and treatment of osteoporosis. Washington (DC): National Osteoporosis Foundation; Apr. 2003 37; http://www.guideline.gov/summary/summary.aspx?doc_id=3862&nbr=003073&string=osteoporosis).

F. Cosman, The Prevention and Treatment of Osteoporosis: A Review, Medscape General Medicine, http://ww.mwdscape.com/viewpoint/4011_pnt, p. 11.

S. Pelarg and G. H. Posner, "Vitamin D Analogs as Modulators of Vitamin D Receptor Action," *Curr. Top. Med. Chem.* 2003 3:1555-1572.

J. Bostrom et al., "Do Structurally Similar Ligands Bind in a Similar Fashion?", *J. Med. Chem.* 2006 49(23):6716-6725.

R. Bouillon et al., Biological Activity of Dihydroxylated 19-Nor-(Pre)Vitamin D3, *J. Bone Miner. Res.* 1993 8(8):1009-1015.

C. J. Rosen, "Osteoporosis" In *Conn's Current Therapy 2005*, R. E Rakel and E. T. Bope, Eds; Elsevier Sanders, Philadelphia, Pa, 2005, p. 700.

Prous ScienceIntegrity Database Search.

PharmaProjects Database Search.

* cited by examiner

METHODS OF TREATMENT USING 3-DESOXY VITAMIN D3 ANALOGS

CROSS-REFERENCE

This application claims the benefit of priority of U.S. Provisional Patent Application Ser. No. 60/323,870, filed Sep. 21, 2001, which is incorporated herein by reference in its entirety.

FIELD OF THE INVENTION

This invention relates to methods for treating a variety of diseases using Vitamin $D_3$ analogs and methods for producing these analogs.

BACKGROUND OF THE INVENTION

Osteoporosis

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are at risk for idiopathic osteoporosis (postmenopausal or Type I osteoporosis); another particularly high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemo-therapy, hyperprolactinemia, anorexia nervosa, primary and secondary amenorrhea, transplant immunosuppression, and oophorectomy. Postmenopausal osteoporosis is characterized by fractures of the spine, while femoral neck fractures are the dominant features of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, osteoclasts and osteoblasts function so that bone formation and bone resorption are in balance. However, in osteoporotics an imbalance in the bone remodeling process develops which results in bone being replaced at a slower rate than it is being lost. Although this imbalance occurs to some extent in most individuals as they age, it is much more severe and occurs at a younger age in postmenopausal osteoporotics, following oophorectomy, or in iatrogenic situations such as those resulting from corticosteroid therapy or the immunosuppression practiced in organ transplantation.

Various approaches have been suggested for increasing bone mass in humans afflicted with osteoporosis, including administration of androgens, fluoride salts, and parathyroid hormone and modified versions of parathyroid hormone. It has also been suggested that bisphosphonates, calcitonin, calcium, 1,25-dihydroxy vitamin $D_3$ and some of its analogs, and/or estrogens, alone or in combination, may be useful for preserving existing bone mass.

Vitamin $D_3$ is a critical element in the metabolism of calcium, promoting intestinal absorption of calcium and phosphorus, maintaining adequate serum levels of calcium and phosphorus, and stimulating flux of calcium into and out of bone. Vitamin $D_3$ is hydroxylated in vivo, with the resulting $1\alpha,25$-dihydroxy metabolite being the active material. Animal studies with $1,25$-$(OH)_2$ vitamin $D_3$ have suggested bone anabolic activity. Aerssens et al. in *Calcif Tissue Int*, 55:443-450 (1994) reported upon the effect of $1\alpha$-hydroxy Vitamin $D_3$ on bone strength and composition in growing rats with and without corticosteroid treatment. However, human usage is restricted to antiresorption due to the poor therapeutic ratio (hypercalciuria and hypercalcemia as well as nephrotoxicity).

Dechant and Goa, in "Calcitriol. A review of its use in the treatment of postmenopausal osteoporosis and its potential in corticosteroid-induced osteoporosis," Drugs Aging [NEW ZEALAND 5 (4): 300-17 (1994)], reported that 1,25-dihydroxyvitamin $D_3$ (calcitriol) has shown efficacy in the treatment of postmenopausal osteoporosis (and promise in corticosteroid-induced osteoporosis) based upon a clinical trial in 622 women with postmenopausal osteoporosis. Patients with mild to moderate disease (but not those with more severe disease) who received calcitriol (0.25 microgram twice daily) had a significant 3-fold lower rate of new vertebral fractures after 3 years of treatment compared with patients receiving elemental calcium 1000 mg/day. In patients commencing long term treatment with prednisone or prednisolone, calcitriol 0.5 to 1.0 micrograms/day plus calcium 1000 mg/day, administered with or without intranasal calcitonin 400 IU/day, prevented steroid-induced bone loss. Overall, calcitriol was well tolerated. At recommended dosages hypercalcaemia was infrequent and mild, generally responding to reductions in calcium intake and/or calcitriol dosage. However, the narrow therapeutic window of calcitriol required that its use be adequately supervised, with periodic monitoring of serum calcium and creatinine levels. This study clearly identifies the key limitation of calcitriol therapy as the close proximity of therapeutic and toxic doses.

Certain 3-desoxy-20-cyclopropyl vitamin D3 analogs are disclosed as inhibiting cellular proliferation in vitro in prostate cancer lines ("20-Cyclopropyl-Cholecalciferol Vitamin D3 Analogs," M. Koike et. al., *Anticancer Research*, 19:1689-1698 (1999))

Hyperparathyroidism

Secondary hyperparathyroidism is a common finding in patients with chronic renal failure. It is established that the reduction of renal $1,25(OH)_2$ vitamin $D_3$ (calcitriol) synthesis is one of the principal mechanisms leading to the secondary hyperparathyroidism in these patients and it has been shown that calcitriol possesses direct suppressive action on PTH synthesis. Therefore, administration of calcitriol has been recommended for the treatment of secondary hyperparathyroidism in these patients. However, as described above, calcitriol has potent hypercalcemic effects giving it a narrow therapeutic window which limits its usage, especially at high doses. It would therefore be desirable to have an alternative means of treating hyperparathyroidism without incurring these undesirable hypercalcemic effects.

While a variety of compounds are available for treating these and other diseases, many of these compounds have undesirable side-effects and/or are relatively unstable, i.e., have short storage period. Therefore, there is a continuing needs for other compounds which are useful in treating these diseases.

SUMMARY OF THE INVENTION

It has been surprisingly discovered that certain 3-desoxy-1α-hdroxy-20-cyclopropyl cholecalciferol vitamin D3 compounds, hitherto known only for their anti-proliferative activity are surprisingly efficacious relative to 1,25-dihydroxy vitamin D3 in increasing bone formation. Accordingly, one aspect of the present invention provides a method for treating osteoporosis or hyperparathyroidism comprising administering a 3-desoxy-1α-hydroxy vitamin $D_3$ analog to the patient, wherein said 3-desoxy vitamin $D_3$ analog is of the formula:

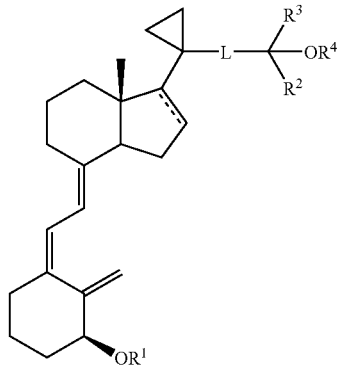

a prodrug or a salt thereof,
wherein
dotted line is optionally a double bond;
L is a linker selected from the group consisting of:

—CH$_2$—CH$_2$—CH$_2$—,

—CH$_2$—CH=CH—,

—CH$_2$—C≡C—,

—CH$_2$—CH$_2$—C(=O)—, and

—CH=CH—CH=CH—;

each of $R^1$ and $R^4$ is selected from the group consisting of hydrogen and alkyl; and
each of $R^2$ and $R^3$ is independently selected from the group consisting of alkyl and haloalkyl, or $R^2$ and $R^3$ and together with the carbon atom to which they are attached to form a cycloalkyl.

Another aspect of the present invention provides a method for producing a compound of the formula:

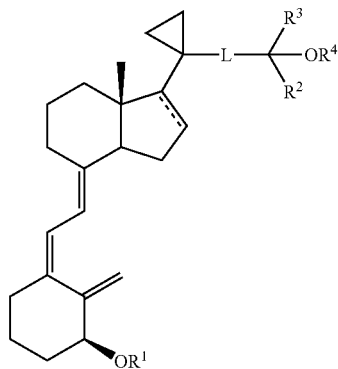

comprising contacting a ketone of the formula:

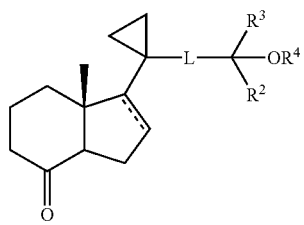

with a phosphine oxide compound of the formula:

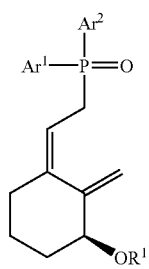

under conditions sufficient to produce said compound of Formula I,
wherein
each of $Ar^1$ and $Ar^2$ is independently optionally substituted aryl;
dotted line is optionally a double bond;
L is a linker selected from the group consisting of:

—CH$_2$—CH$_2$—CH$_2$—,

—CH$_2$—CH=CH—,

—CH$_2$—C≡C—,

—CH$_2$—CH$_2$—C(=O)—, and

—CH=CH—CH=CH—;

each of $R^1$ and $R^4$ is selected from the group consisting of hydrogen, alkyl, and a hydroxy protecting group; and each of $R^2$ and $R^3$ is independently selected from the group consisting of alkyl; haloalkyl; or $R^2$ and $R^3$ and together with the carbon atom to which they are attached to form a cycloalkyl.

In one embodiment of the present method for producing a compound of Formula I, $R^4$ is hydrogen. In a particular embodiment, the method further comprises the steps of protecting the hydroxy group of said ketone of Formula II prior to said step of contacting with said phosphine oxide compound of Formula III and removing the hydroxy protecting group after contacting said ketone of Formula II with said phosphine oxide compound of Formula III to produce said compound of Formula I.

DETAILED DESCRIPTION OF THE INVENTION

Definitions

"Alkyl" means a linear fully-saturated hydrocarbon radical having one to six carbon atoms or a branched fully saturated hydrocarbon radical having three to six carbon atoms.

"Haloalkyl" refers to an alkyl radical, as defined above, in which one or more hydrogen atoms attached to the carbon backbone have been replaced with one or more halides. Preferred halide is fluoride.

"Cycloalkyl" means a fully saturated cyclic hydrocarbon radical of three to six ring carbon atoms, e.g., cyclopropyl, cyclopentyl and the like.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy group in compound (I) is bonded to any group that may be cleaved in vivo to regenerate the free hydroxyl group. Examples of prodrugs include, but are not limited to esters (e.g., acetate, formate, and benzoate derivatives), carbamates (e.g., N,N-dimethylaminocarbonyl) and ethers of hydroxy functional groups in compounds of Formula (I), and the like. Such compounds are routinely made by one of skill in the art by acylating or etherifying the hydroxy group in the parent molecule.

"Hydroxy protecting group" refers to a grouping of atoms that when attached to a hydroxy group in a molecule masks, reduces or prevents the reactivity of the hydroxy group. Examples of protecting groups can be found in T. W. Green and P. G. Futs, *Protective Groups in Organic Chemistry*, (Wiley, 2$^{nd}$ ed. 1999) and Harrison and Harrison et al., *Compendium of Synthetic Organic Methods*, Vols. 1-8 (John Wiley and Sons, 1971-1996). Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Therapeutically effective amount" means the amount of a compound that, when administered to a mammal for treating or preventing a disease, is sufficient to effect such treatment or prevention for the disease. The "therapeutically effective amount" will vary depending on the compound, the disease and its severity and the age, weight, etc., of the patient to be treated.

"Treating" or "treatment" of a disease includes: (1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

When referring to a chemical reaction, the terms "treating", "contacting" and "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

General Description

In one aspect, the present invention is directed to a method for treating osteoporosis, hyperparathyroidism or an autoimmune disease in a patient by administering a 3-desoxy vitamin $D_3$ analog of Formula I, where $R^1$, $R^2$, $R^3$, $R^4$ and L are as defined in the Summary of the Invention.

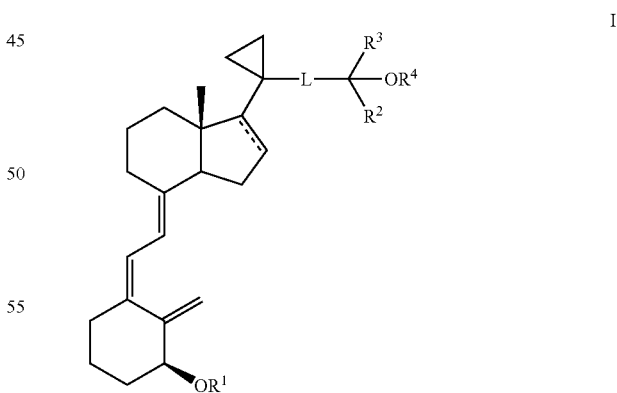

When the cyclopentane ring moiety of Formula I does not contain a double bond, i.e., when the dotted line is absent or is not a double bond, the stereochemistry of the side chain on the cyclopentane ring system can be alpha or beta. Preferably, the stereochemistry of the side chain on the cyclopentane ring system is beta, i.e., of the formula:

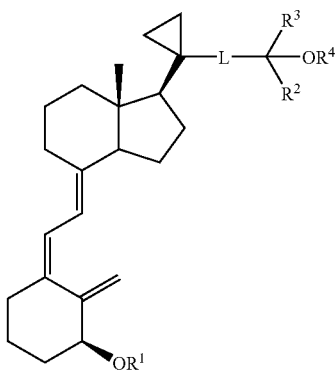

In one embodiment, the 3-desoxy vitamin $D_3$ analog is the formula:

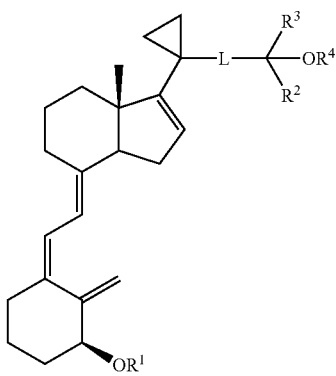

where $R^1$, $R^2$, $R^3$, $R^4$ and L are as defined in the Summary of the Invention.

In yet another embodiment, the linker L is selected from the group consisting of: $-CH_2-CH_2-CH_2-$; $-CH_2-CH=CH-$; $-CH_2-C\equiv C-$; and $-CH=CH-CH=CH-$. Preferably, L is $-CH_2-CH=CH-$; $-CH_2-C\equiv C-$. More preferably L is $-CH_2-CH=CH-$ where the double is trans.

In another embodiment, preferably $R^1$ is hydrogen.

In another embodiment, preferably $R^4$ is hydrogen.

In another embodiment, both $R^1$ and $R^4$ are hydrogen.

Still in another particular embodiment, each of $R^2$ and $R^3$ is independently alkyl or haloalkyl, preferably methyl or trifluoromethyl.

A number of different substituent preferences have been given above and following any of these substituent preferences results in a compound of the invention that is more preferred than one in which the particular substituent preference is not followed. However, these substituent preferences are generally independent, although some preferences are mutually exclusive, and following more than one of these preferences may result in a more preferred compound than one in which fewer of the substituent preferences are followed.

5   General Synthetic Scheme for Preparation of Compounds of Formula I

While a variety of synthetic methodologies are available for preparation of compounds of Formula I, one particular embodiment for preparing compounds of Formula I is illustrated below.

Compounds of Formula I can be prepared from compounds of Formula II,

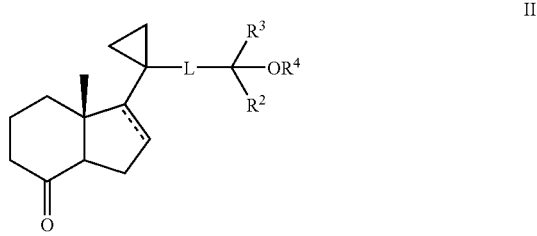

by reaction with a phosphine oxide compound of the formula:

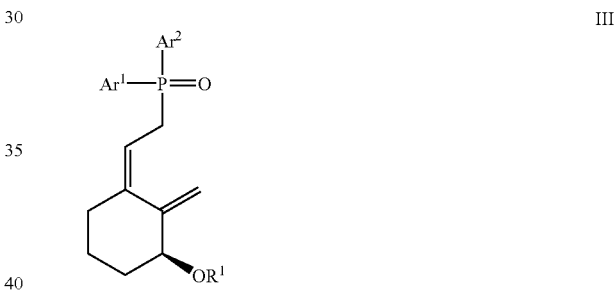

where each of $Ar^1$ and $Ar^2$ is independently optionally substituted aryl, and the dotted line, $R^1$, $R^2$, $R^3$, $R^4$ and L are as defined in the Summary of the Invention. Preferably, $Ar^1$ and $Ar^2$ are phenyl. When $R^1$ and/or $R^4$ are hydrogen, the corresponding hydroxy groups are preferably protected with hydroxy protecting groups that are compatible with the coupling reaction conditions prior to the coupling reaction between the ketone of Formula II and the phosphine oxide compound of Formula III. Suitable hydroxy protecting groups are well known to one of ordinary skill in the art and examples of such hydroxy protecting groups are disclosed in *Protective Groups in Organic Synthesis,* 3rd edition, T. W. Greene and P. G. M. Wuts, John Wiley & Sons, New York, 1999, and Harrison and Harrison et al., *Compendium of Synthetic Organic Methods,* Vols. 1-8 (John Wiley and Sons, 1971-1996), which are incorporated herein by reference in their entirety. Representative hydroxy protecting groups include benzyl and trityl ethers, tetrahydropyranyl ethers, trialkylsilyl ethers and allyl ethers.

Typically, hydroxy groups are protected as silylethers; however, the scope of the invention includes the use of alternative hydroxyl protecting groups known in the art as described in the above disclosed *Protective Groups in Organic Synthesis,* 3rd edition, and *Compendium of Synthetic Organic Methods,* Vols. 1-8.

In general, a phosphine oxide compound of Formula III in tetrahydrofuran is reacted with n-butyllithium typically at about −78° C. To this mixture is then added solution of a ketone of Formula II in tetrahydrofuran to provide a compound of Formula I. As stated above, when $R^1$ and/or $R^4$ are hydrogen, they are protected with hydroxy protecting groups prior to the coupling reaction. In such a case, the hydroxy protecting groups are then removed to provide a compound of Formula I.

Synthesis and purification of compounds of Formula III are known and conventional in this art. See, for example, M. R. Uskokovic et al. "Vitamin D Gene Regulation, Structure Function Analysis and Clinical Application," Paris, France, pp 139-145 (1991), U.S. Pat. Nos., 5,086,191 and 5,616,759 to DeLuca et al., U.S. Pat. No. 5,087,619 to Baggiolini et al., U.S. Pat. No. 5,384,314 to Doran et al., U.S. Pat. No. 5,428,029 to Doran et al., U.S. Pat. No. 5,451,574 to Baggiolini et al.; European patent publication EP 0 808,832 A2, patent publication WO 96/31216 to Brasitus et al.; Shiuey et al., *J. Org. Chem.*, 55:243-247 (1990), Kiegel, J. et al. and *Tetr. Lett.*, 32:6057-6060 (1991), Perlman, K. L., et al., *Tetr. Lett.*, 32:7663-7666 (1991).

Reaction Scheme I illustrates a synthetic method for preparing a compound of Formula IA.

dihydroxy-20,20-dialkyl vitamin D3 analogs). The compound of Formula IV is converted to the compound of Formula V by selective partial reduction of the triple bond to an E-double bond using lithium aluminum hydride in inert organic acid such as tetrahydrofuran. The reaction is typically conducted by adding the compound of Formula IV to a suspension of $LiAlH_4$ in THF at 0° C. or 5° C. The reaction mixture is heated under refluxing condition to provide the compound of Formula V. The compound of Formula V is converted to the ketone compound of Formula VI by oxidation using an oxidizing agent such as pyridinium dichromate. The reaction is generally conducted in a halogenated solvent such as methylene chloride at room temperature. The hydroxy group of compound of Formula VI is then protected as a silyl ether of Formula VII using a silylating agent, such as 1-(trimethylsilyl)imidazole, trimethylsilyl chloride or trimethylsilyl triflate, in an inert solvent, such as a halogenated solvent (e.g., methylene chloride), at room temperature. The compound of Formula IIIa is reacted with n-butyllithium and the resulting compound is reacted with the compound of Formula VII in tetrahydrofuran at a temperature of −78° C. to give the compound of Formula IA after removal of silyl protecting groups, for example, with tetrabutylammonium fluoride in tetrahydrofuran solvent.

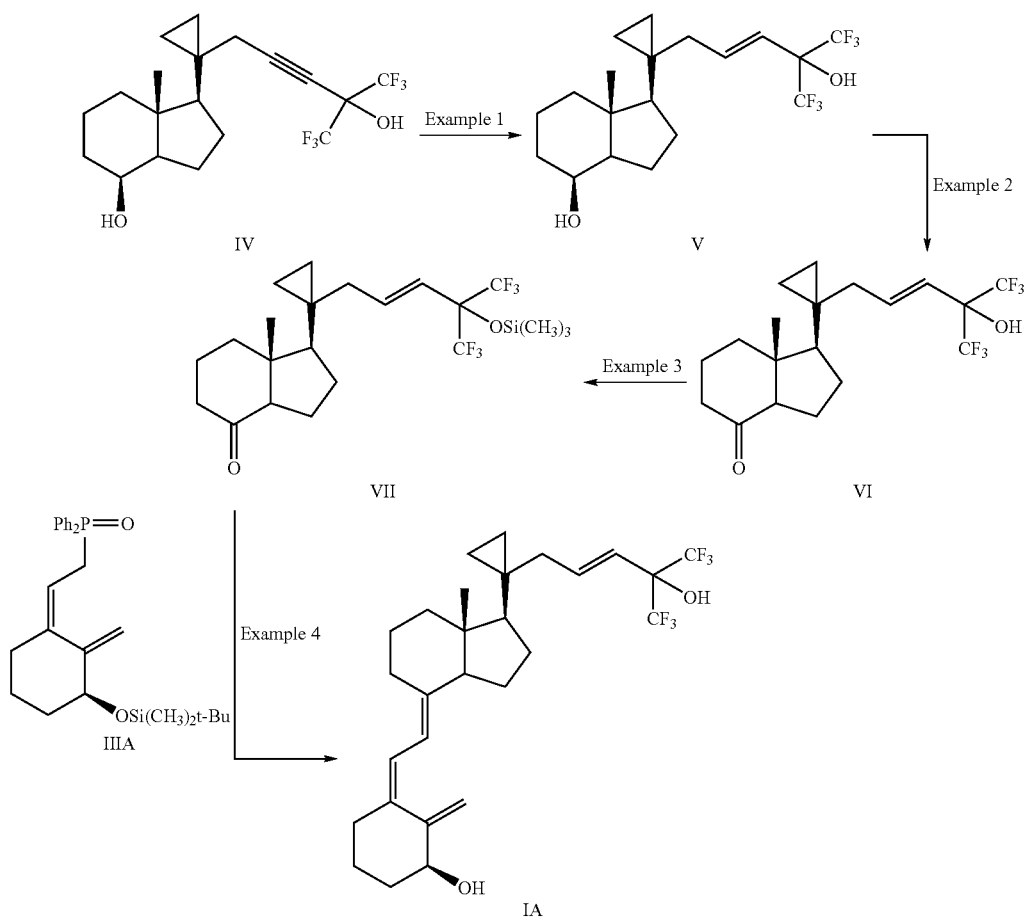

In Reaction Scheme 1, the compound of Formula IV is a known compound prepared by the method described in WO99/12894, published Mar. 18, 1999 (Preparation of 1,3-

Similarly, a Z-stereoisomer analog or a saturated carbon chain analog of compound of Formula IA can be prepared by reduction of the compound of Formula IV with hydrogen in the presence of an appropriate hydrogenation catalyst, such as Pd—S or Pd, respectively. The resulting compounds can be subjected to similar reaction conditions as shown in Scheme I to produce the corresponding a Z-isomer analog and a saturated carbon chain analog of the compound of Formula IA.

As shown in Reaction Scheme 2, a compound of Formula II comprising an acetylenic alcohol and varying alkyl, haloalkyl and cycloalkyl groups of R and R can be prepared by condensing an acetylide anion derived from a compound of Formula VIII (where Pg is a hydroxy protecting group) with an appropriate ketone, haloketone (e.g. hexafluoroacetone) and cycloketone, and removing the protecting group.

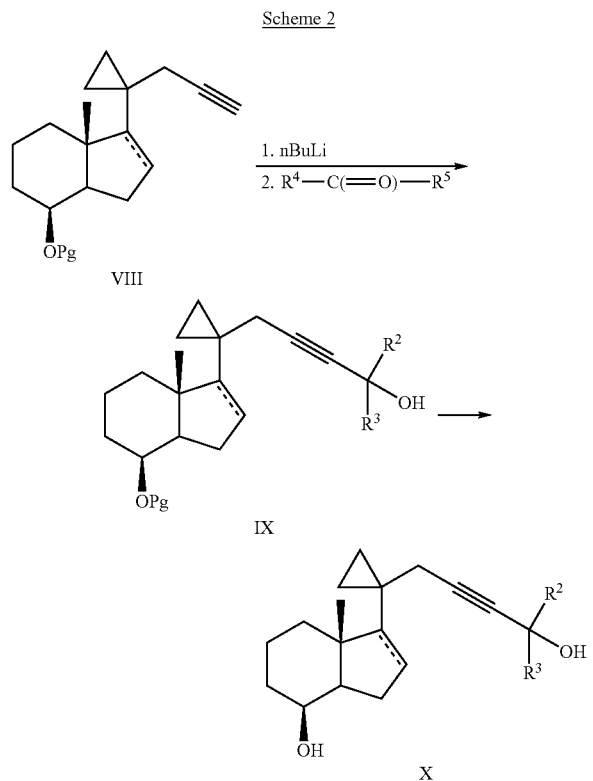

The compound of Formula X is then subjected to a similar reaction conditions shown above in Reaction Scheme I (i.e., oxidation, protection and coupling) to produce a compound of Formula I having an acetylenic linker moiety.

Utility

The compounds of the present invention are useful for the prevention and treatment of a variety of mammalian conditions manifested by loss of bone mass All such conditions are referred to as "bone-related diseases" and are described in more detail hereunder. In particular, the compounds of this invention are indicated for the prophylaxis and therapeutic treatment of osteoporosis and osteopenia in mammals without inducing hypercalciuria, hypercalcemia, or nephrotoxicity. "Hypercalcemia" is an excessive concentration of calcium in the serum; in humans (and rats) this corresponds to greater than about 10.5 mg/dl. "Intolerable hypercalcemia", usually occurring at serum calcium concentrations greater than about 12 mg/dl, is associated with emotional lability, confusion, delirium, psychosis, stupor, and coma.

The compounds of the present invention are useful in the treatment of Type I (postmenopausal), Type II (iatrogenic), and Type III (senile) osteoporosis, including that associated with immunosuppressive drugs used in organ transplantation and that associated with corticosteroid treatment (e.g. for asthma), as well in the treatment of osteodystrophy due to renal dialysis and hyperparathyroidism. Treatment with the 3-desoxy-20-desmethyl-20-cyclopropyl vitamin D3 analogs as described herein results in increased bone mineral density and unlike conventional treatments provides bone of good quality. Therefore, the treatments described herein may reduce the incidence of fracture and result in faster healing of pre-existing fractures. Such treatments are particularly useful for patients suffering from estrogen withdrawal (e.g. elderly females) who would otherwise be at risk for an increased fracture rate. Types of fractures treatable include both traumatic and osteoporotic fractures, e.g., fractures of the hip, neck of the femur, wrist, vertebrae, spine, ribs, sternum, larynx and trachea, radius/ulna, tibia, patella, clavicle, pelvis, humerus, lower leg, fingers and toes, face and ankle.

The compounds of the present invention are also useful in treating diseases caused by elevated levels of parathyroid hormone. In one aspect, compounds of the invention are used in treating secondary hyperparathyroidism associated with renal failure and in particular with reversing or reducing the bone loss associated with renal insufficiency. Other aspects include the treatment of renal osteodystrophy associated with late stage secondary hyperparathyroidism. Other aspects include the treatment of primary hyperparathyroidism.

Generally, compounds of the present invention do not cause the elevated calcium levels observed with other vitamin $D_3$ analogs such as 1,25 $(OH)_2$ vitamin $D_3$, thus providing an improved therapeutic ratio and better treatment of the above diseases.

Administration & Pharmaceutical Compositions

In general, the compound of this invention may be administered in amounts between about 0.0002 and 0.5 mg compound/kg body weight per day, preferably from about 0.001 to about 0.1 mg/kg body weight per day, more preferably from about 0.002 to about 0.02 mg/kg body weight per day, most preferably from about 0.005 to about 0.010 mg/kg body weight per day. For a 50 kg human subject, the daily dose of active ingredient may be from about 0.01 to about 25 μg, preferably from about 0.05 to about 10 μg, most preferably from about 1.0 μg to about 10 μg per day. This dosage can be delivered in a conventional pharmaceutical composition by a single administration, by multiple applications, or via controlled release, as needed to achieve the most effective results, preferably once or twice daily by mouth. In certain situations, alternate day dosing can prove adequate to achieve the desired therapeutic response.

The selection of the exact dose and composition and the most appropriate delivery regimen are influenced by, inter alia, the pharmacological properties of the formulation, the nature and severity of the condition being treated, and the physical condition and mental acuity of the recipient.

Representative delivery regimens include oral, parenteral (including subcutaneous, intramuscular and intravenous), rectal, buccal (including sublingual), pulmonary, transdermal, and intranasal, most preferably oral. Administration can be continuous or intermittent (e.g., by bolus injection).

A related aspect of this invention relates to combination therapies of compounds of Formula I with other active agents such as bisphosphonates, estrogen, SERMS (selective estrogen receptor modulators), calcitonins or anabolic therapies. Examples of bisphosphonates include alendronate, ibandronate, pamidronate, etidronate and risedronate. Examples of SERMS include raloxifene, dihydroraloxifene and lasofoxifene. Calcitonins include human and salmon calcitonin. Anabolic agents include parathyroid hormones (PTH) e.g. hPTH (1-34), PTH(1-84), and parathyroid hormone-related protein (PTHrP) and analogs thereof. Particular analogs of PTHrP are described in "Mono- and Bicyclic Analogs of Parathyroid Hormone-Related Protein. 1. Synthesis and Biological Studies," Michael Chorev et al. Biochemistry, 36:3293-3299 (1997) and "Cyclic analogs of PTH and PTHrP," WO 96/40193 and U.S. Pat. No. 5,589,452 and WO 97/07815. The other active agent may be administered concurrently, prior to or after the compound of Formula I and may be administered by a different delivery method.

A further aspect of the present invention relates to pharmaceutical compositions comprising a compound of the present invention as an active ingredient in admixture with a pharmaceutically acceptable non-toxic carrier. As mentioned above, such compositions can be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions of the present invention can conveniently be administered in unit dosage form and can be prepared by any of the methods well-known in the pharmaceutical art, for example, as described in *Remington's Pharmaceutical Sciences,* 17th ed., Mack Publishing Company, Easton, Pa. (1985). Formulations for parenteral administration can contain as excipients sterile water or saline, alkylene glycols such as propylene glycol, polyalkylene glycols such as polyethylene glycol, oils of vegetable origin, hydrogenated naphthalenes and the like. Formulations for nasal administration can be solid and can contain excipients, for example, lactose or dextran, or can be aqueous or oily solutions for use in the form of nasal drops or metered spray. For buccal administration typical excipients include sugars, calcium stearate, magnesium stearate, pregelatinated starch, and the like.

Orally administrable compositions can comprise one or more physiologically compatible carriers and/or excipients and can be in solid or liquid form. Tablets and capsules can be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions can contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions can be encapsulated in, for example, gelatin to provide a unit dosage form.

Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; *Pharmaceutical Technology,* 9, (1985). Some of the advantages of using SEG capsules are: a) dose-content uniformity is optimized in SEG capsules because the drug is dissolved or dispersed in a liquid that can be dosed into the capsules accurately, b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area, and c) degradation of drugs that are sensitive to oxidation during long-term storage is prevented because the dry shell of soft gelatin provides a barrier against the diffusion of oxygen.

The dry shell formulation typically comprises of about 40% to 60% concentration of gelatin, about a 20% to 30% concentration of plasticizer (such as glycerin, sorbitol or propylene glycol) and about a 30 to 40% concentration of water. Other materials such as preservatives, dyes, opacifiers and flavours also can be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

The following examples are given to enable those skilled in the art to more clearly understand and to practice the present invention. They should not be considered as limiting the scope of the invention, but merely as being illustrative and representative thereof.

EXAMPLES

The following examples are offered to illustrate, but not to limit the claimed invention.

Example 1

This example illustrate a method for producing [1R-(1α (E),3aβ,7aα)]-Octahydro-7a-methyl-1-[5,5,5-trifluoro-4-hydroxy-4-(trifluoromethyl)-2-pentynyl]cyclopropyl]-4H-inden-4-ol.

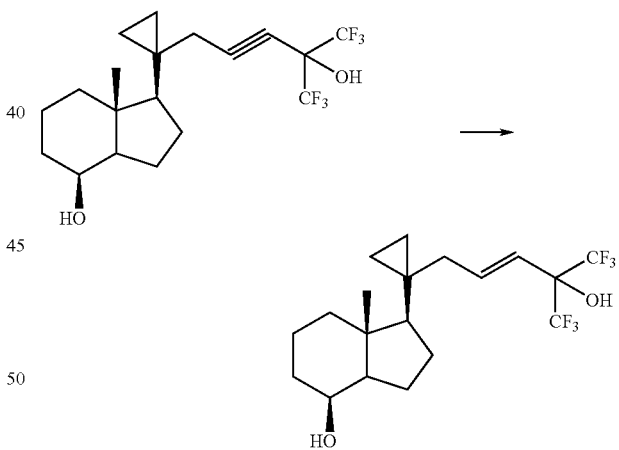

To a stirred, chilled (5° C.) suspension of LiAlH$_4$ (237.2 mg; 6.25 mmol) in anhyd. THF (6.0 ml) was added powdered NaOMe (338 mg, 6.25 mmol). The mixture was stirred under Ar at 5° C. for 15 min, treated with a solution of [1R-(1α,3aβ, 4α,7aα)]-octahydro-7a-methyl-1-[1-[5,5,5-trifluoro-4-hydroxy-4-(trifluoromethyl)-2-pentynyl]cyclopropyl]-4H-inden-4-ol (500 mg, 1.25 mmol) in anhyd THF (6.0 ml), and then boiled under reflux for 2.5 h. After cooling, the mixture was diluted with Et$_2$O (25 ml), quenched by the drop-wise addition of water (2.0 ml) and 2 M NaOH (2.0 ml), and stirred at room temperature for 30 min. MgSO$_4$ (5 g) was added, and after an additional 30 min of stirring, the mixture was diluted with Et$_2$O (25 ml) and filtered over Celite (15 g), which was washed with EtOAc (3×20 ml). Evaporation gave a gum (508 mg), which was purified by flash chromatography (50 g of silica gel, 3.5 cm diameter column, 30% EtOAc in hexanes), taking 20-ml fractions. Evaporation of fractions 7-12 gave colorless crystals (486 mg), which were triturated with hexane and collected by filtration to give the title compound (442 mg, 88%): mp 122-123° C.; $[\alpha]_D$+42.1° (EtOH, c=0.80); IR 3540, 1602, 965 cm$^{-1}$; $^1$H NMR δ 0.05 (1 H, m), 0.27 (1 H, m), 0.34 (1 H, m), 0.74 (1 H, m), 0.98 (1 H, m), 1.00 (3 H, s), 1.17-1.25 (2 H, m), 1.35-1.60 (6 H, m), 1.65 (1 H, dd, J=12, 5), 1.75-1.87 (3 H, m), 2.02 (1 H, d, J=11), 2.78 (1 H, dd, J=14, 8.5), 2.92 (1 H, s, OH), 4.05 (1 H, br s), 5.59 (1 H, d, J=16), 6.30 (1 H, ddd, J=16, 8.5, 6); MS m/z 400 (M$^+$, 10). Anal. Calcd for $C_{19}H_{26}F_6O_2$: C, 56.99; H, 6.55; F, 28.47. Found: C, 56.87; H, 6.33; F, 28.69.

Example 2

This example illustrate a method for producing [1R-(1α (E), 3aβ,7aα)]]Octahydro-7a-methyl-1-[1-[1-[5,5,5-trifluoro-4-hydroxy-4-(trifluoromethyl)-2-pentynyl]cyclopropyl]-4H-inden-4-one.

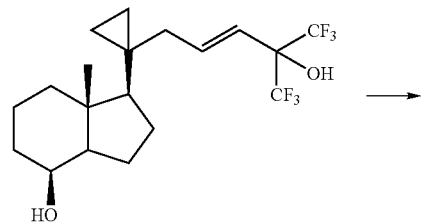

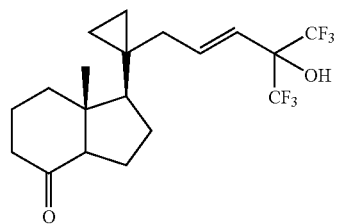

To a stirred solution of [1R-(1α(E),3aβ,4α,7aα)]]octahydro-7a-methyl-1-[5,5,5-trifluoro-4-hydroxy-4-(trifluoromethyl)-2-pentynyl]cyclopropyl]-4H-inden-4-ol (400 mg, 1.00 mmol) in CH$_2$Cl$_2$ (8.0 ml) was added pulverized pyridinium dichromate (1.25 g, 3.3 mmol). The mixture was stirred at room temperature for 4.5 h, diluted with diisopropyl ether (15 ml), and worked up to give 395 mg of a colorless gum. Flash chromatography of which (50 g of silica gel, 3.5 cm diameter column, 30% EtOAc in hexanes), collecting 20-ml fractions, gave after evaporation of fractions 7-12, the title compound (376 mg, 94%) as colorless crystals: mp 79-80° C.; $[\alpha]_D$+6.9° (EtOH, c=1.00); IR 3334, 1704, 964 cm$^{-1}$; $^1$H NMR δ 0.14 (1 H, m), 0.33 (1 H, m), 0.69 (1 H, m), 0.70 (3 H, s), 1.46-1.80 (5 H, m), 1.91-2.30 (6 H, m), 2.44 (1 H, dd, J=11, 6), 2.74 (1 H, dd, J=15, 8.5), 2.98 (1 H, s, OH), 5.62 (1 H, d, J=15), 6.33 (1 H, ddd, J=15, 8.5, 6); MS m/z 398 (M$^+$, 20) Anal. Calcd for $C_{19}H_{24}F_6O_2$: C, 57.28. H, 6.07; F, 28.61. Found: C, 57.19; H, 6.25; F, 28.71.

Example 3

This example illustrates a method for producing [1R-[1α (E),3aβ,7aα)]]-Octahydro-7a-methyl-1-[1-[5,5,5-trifluoro-4-trifluoromethyl)-4-[(trimethylsilyl)oxy]-2-pentynyl]cyclopropyl]-4H-inden-4-one.

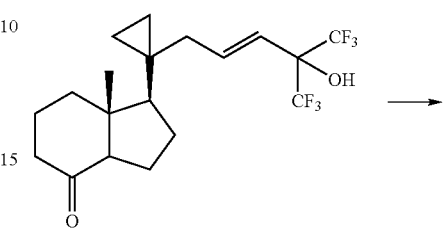

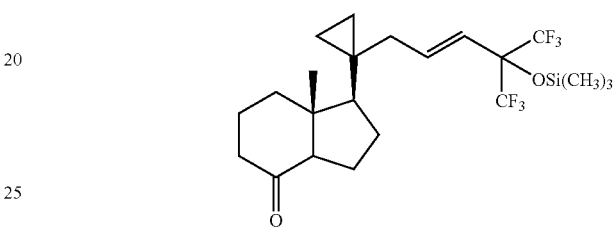

A stirred solution of [1R-(1α)(E),3aβ,7aα)]]-octahydro-7a-methyl-1-[1-[5,5,5-trifluoro-4-hydroxy-4-trifluoromethyl)-2-pentynyl]cyclopropyl]-4H-inden-4-one (165 mg, 0.41 mmol) in anhyd CH$_2$Cl$_2$ (5 ml) was reacted with 1-(trimethylsilyl)imidazole (0.5 ml, 3.4 mmol) during 5 h to give after work up crude title compound (193 mg,). Flash chromatography (25 g of silica gel, 20% EtOAc in hexanes) gave the title compound (161 mg, 83%) as an oil: $[\alpha]_D$+3.4° CHCl$_3$, c=1.0); IR 1706 cm$^{-1}$; $^1$H NMR δ 0.13 (1 H, m), 0.22 (9 H, s), 0.32(1 H, m), 0.67 (1 H, m), 0.70 (3 H, s), 1.10 (1 H, m), 1.50-2.40 (11 H, m), 2.44 (1 H, dd, J=11, 6), 2.68 (1 H, dd, J=16, 8.5), 5.57 (1 H, d, J=16), 6.16 (1 H, ddd, J=16, 8.5, 6); MS m/z 470 (M$^+$, 33). Anal. Calcd for $C_{22}H_{32}F_6O_2Si$: C, 56.15; H, 6.85; F, 24.22. Found: C, 56.42; H, 6.63; F, 24.37.

Example 4

This example illustrates a method for producing 3-Desoxy-1,25-dihydroxy-20-methyl-23-(E)-ene-26,27-hexafluoro-21,28-cyclocholecalciferol.

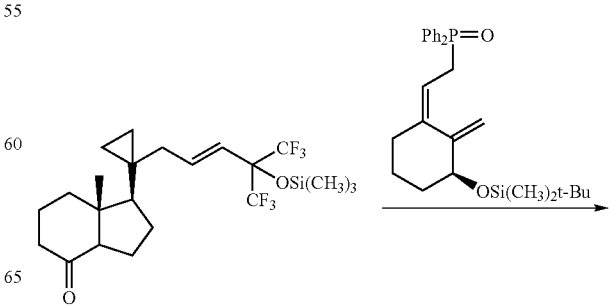

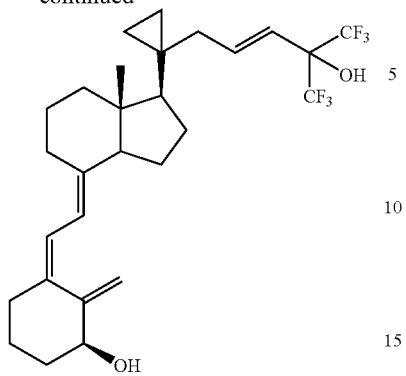

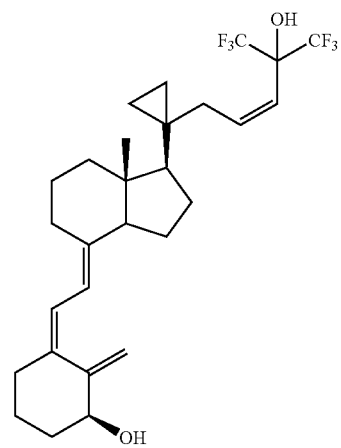

Horner reagent [R-(Z)]-[2-[3-[[(1,1-dimethylethyl)-dimethyl-silyl]oxy]-2-methylenecyclohexylidene]ethyl]diphenylphosphine oxide (395 mg, 0.872 mmol) in anhydrous THF (5.0 ml) was deprotonated with a 1.6 M solution of n-BuLi in hexanes (0.55 ml, 0.88 mmol) at −78° C. and after 8 min reacted with ketone [1S-[1α(E),3aβ,7aα]]octahydro-7a-methyl-1-[1-[5,5,5-trifluoro-4-(trifluoromethyl)-4-[trimethylsilyl)oxy-2-pentenyl]cyclopropyl]-4H-inden-4-one (170 mg, 0.361 mmol) in anhyd THF (2.0 ml) during 3 h and worked up. Flash chromatography (45 g of silica gel, 20% EtOAc in hexanes) gave a gum (215 mg). This was dissolved in THF (3 ml), treated with 1.0 M solution of n-Bu$_4$N$^+$F$^-$ in THF (2.8 ml) and stirred for 19 h. Work up followed by flash chromatography (40 g silica gel, 40% EtOAc in hexanes)gave a gum, which was dissolved in HCO$_2$Me (5.0 ml), filtered through a 0.45 μm filter and evaporated. High vacuum drying (3 h) gave title compound (144 mg) as a colorless foam: [α]$_D$4.0° (MeOH, c=0.35); UV λ$_{max}$ 265 (ε=15,837), 211 (ε=14,458) nm; IR 3598, 1651 cm$^{-1}$; $^1$H NMR δ 0.11 (1 H, m), 0.29(2 H, m), 0.60 (3 H, s), 0.61 (1 H, m), 1.10 (1 H, m), 1.21-1.35 (1 H, m), 1.50 (6 H, m), 1.70 (2 H, m), 1.90 (2 H, m), 2.00 (3 H, m), 2.30 (2 H, m), 2.60 (1 H, d, J=12), 2.85 (2 H, m), 2.90 (1 H, s), 4.22 (1 H, s), 4.42 (1 H, s), 4.99 (1 H, s), 5.32 (1 H, s), 5.42 (1 H, d, J=12), 5.99 (1 H, d, J=11), 6.10(1 H, ddd, J=12, 7, 6), 6.36(1 H, d, J=11); MS (FAB) m/z 535 (M$^+$+H).

Example 5

This example illustrates a method for producing 3-Desoxy-1,25-dihydroxy-20-methyl-23-(Z)-ene-26,27-hexafluoro-21,28-cyclocholecalciferol.

Horner reagent [R-(Z)]-2-[3-[[(1,1-dimethylethyl)-dimethylsilyl]oxy]-2-methylenecyclohexylidene]ethyl]diphenylphosphineoxide (236 mg, 0.5 mmol) in THF (3.0 ml) was treated with a 1.6 M solution of n-BuLi in hexanes(0.32 ml, 0.512 mmol). After 8 min, ketone [1S-[1α(Z), 3aβ,7aα]] octahydro-7a-methyl-1-[1-[5,5,5-trifluoro-4-(trifluoromethyl)-4-[(trimethylsilyl)oxy]-2-pentenyl]cyclopropyl-4H-inden-4-one (117.5 mg, 0.25 mmol) in THF (2.0 ml) was added and stirring continued for 2.5 h. Work up gave a gum, which was purified by flash chromatography (40 g of silica gel, 20% EtOAc in hexanes) to give a gum (120 mg). This was dissolved in THF (2.0 ml), treated with a 1 M solution of n-Bu$_4$N$^+$F$^-$ in THF (2.0 ml) and stirred at room temperature for 20 h, and worked up. Flash chromatography (40 g of silica gel, 40% EtOAc in hexanes) gave title compound (29 mg) as a colorless foam: [α]$_D$–41°(MeOH, c=0.14); IR 3569 cm$^{-1}$; UV λ$_{max}$ 214 (10,968), 219 (12,931), 259 (12,818) nm; $^1$H NMR δ 0.02 (1 H, m), 0.32 (2 H, m), 0.60 (1 H, m), 0.61 (3 H, s), 1.1-1.7 (11 H, m), 1.85 (2 H, m), 2.0 (3 H, m), 2.2 (3 H, m), 2.85 (3 H, m), 4.12 (1 H, br s), 4.90 (1 H, s), 5.30 (1 H, s), 5.40 (1 H, d, J=12.8), 6.0 (1 H, d, J=11), 6.12 (1 H, dd, J=12.8, 6.8),6.29(1 H, d, J=11), 6.12 (1 H, dd, J=12.8, 6.8), 6.29 (1 H, d, J=11); MS m/z 518 (M$^+$, 22).

Example 6

This example illustrates a method for producing 3-desoxy-1,25-Dihydroxy-20-methyl-23-yne-21,28-cyclocholecalciferol.

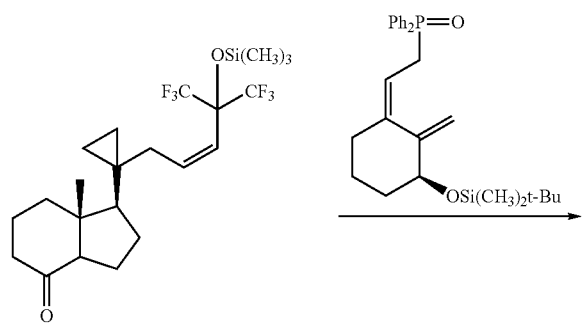

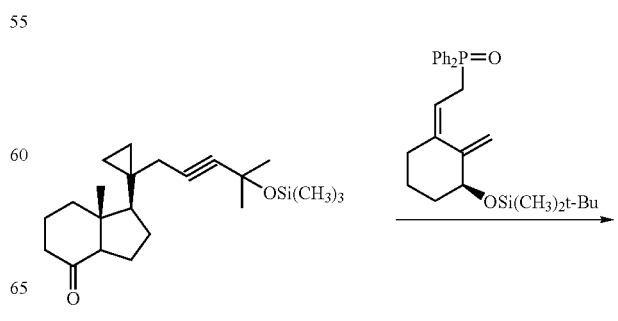

-continued

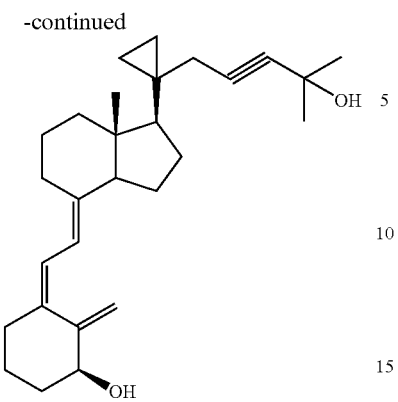

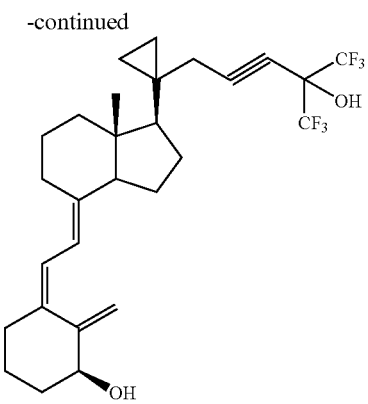

Horner reagent [R-(Z)]-2-[3-[[(1,1-dimethylethyl)dimethylsilyl]oxy]-2-methylenecyclo-hexylidene]ethyl]diphenylphosphine oxide (375 mg, 0.828) in THF (5.0 ml) was treated with 1.6 M solution of n-BuLi in hexanes (0.51 ml, 0.81 mmol). After 8 min, [1R-(1α,3aβ,7aα)]-Octahydro-7a-methyl-1-[4-methyl-4-[(trimethylsilyl)oxy]-2-pentynyl]cyclopropyl]-4H-inden-4-one (180 mg 0.50 mmol) in THF (4.0 ml) was added and the mixture worked up after 3.5 h. Flash chromatography (45 g of silica gel, 7% EtOAc in hexanes) gave a syrup (273 mg), which was dissolved in THF (3.3 ml) and stirred with a 1.0 M solution of n-Bu$_4$N$^+$F$^-$ in THF (3.3 ml) for 28 h, and worked up. Flash chromato-graphy (45 g silica gel, 40% EtOAc in hexanes) gave title compound (114 mg) as a colorless foam: $[\alpha]_D$ –70.32° (EtOH, c=0.539); UV $\lambda_{max}$ 215 ($\epsilon$=13,326), 262 ($\epsilon$=17,661) nm; IR 3601 cm$^{-1}$; $^1$NMR δ 0.28 (2 H, m), 0.41 (1 H, m), 0.59 (1 H, m), 0.60 (3 H, s), 1.10 (1 H, m), 1.50 (6 H, s), 1.55-2.0 (18 H, m), 2.09 (1 H, d, J=17), 2.22 (2 H, m), 2.60 (1 H, d, J=17), 2.80 (1 H, d, J=11), 4.11 (1 H, br s), 4.91 (1 H, s), 5.30 (1 H, s), 5.99 (1 H, d, J=11), 6.27 (1 H, d, J=11); MS m/z 408.3 (M$^+$, 60).

Example 7

This example illustrates a method for producing 3-desoxy-1,25-dihydroxy-20-methyl-23-yne-26,27-hexafluoro-21,28-cyclocholecalciferol.

Homer reagent [R-(Z)]-2-[3-[[(1,1-dimethylethyl)-dimethylsilyl]oxy]-2-methylenecyclohexylidene]ethyl]diphenylphosphineoxide (350 mg, 0.773 mmol) in THF (5.0 ml) was deprotonated with 1.6 M n-BuLi in hexanes (0.49 ml, 0.784 mmol) at –78° C. and after 8 min reacted with ketone [1S-1α,3aβ,7aα)]octahydro-7a-methyl-1-[1-[5,5,5-trifluoro-4-hydroxy-4-(trifluoromethyl)-2-pentynyl]cyclopropyl]-4H-inden-4-one (158 mg, 0.40 mmol) during 3.0 h. Flash chromatography of the crude product (45 g silica gel, 20% EtOAc in hexanes) followed by desilylation during 18 h at room temperature with a 1 M solution of n-Bu$_4$N$^+$F$^-$ in THF (1.8 ml) and flash chromato-graphic purification (45 g silica gel, 40% EtOAc in hexanes) gave title compound (117 mg) as a colorless foam: $[\alpha]_D$ –58.30° (EtOH, c=0.456); UV $\lambda_{max}$ 214 ($\epsilon$=12,900), 260 ($\epsilon$=15,701) nm; $^1$H NMR δ 0.29 (1 H, m), 0.35 (1 H, m), 0.37 (1 H, m) 0.59 (3 H, s), 0.64 (1 H, m), 1.4-1.90 (12 H, m) 2.00 (4 H, m), 2.18 (1 H, d, J=17), 2.25 (2 H, m), 2.72 (1 H, d, J=17), 2.81 (1 H, m), 3.34 (1 H, s, OH), 4.12 (1 H, br s), 4.92 (1 H, s), 5.28 (1 H, s), 5.98 (1 H, d, J=11), 6.27 (1 H, d, J=11); MS m/z 516.2 (M$^+$, 90).

Example 8

This example illustrates a method for producing 3-Desoxy-1,25-dihydroxy-20-methyl-21,28-cyclocholecalciferol.

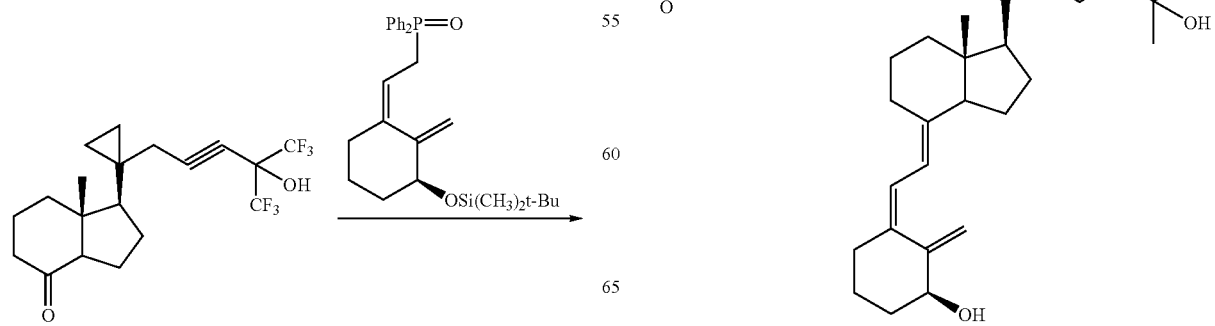

A magnetically stirred 25 ml, 3-neck round bottom flask equipped with a thermometer, a rubber septum on the side and a Claisen adapter containing a nitrogen sweep and rubber septum at the center, was charged with 0.564 gr (1,246 mmol) of [R-(Z)]-2-[3-[[(1,1-dimethylethyl)-dimethylsilyl]oxy]-2-methylenecyclohexylidene]ethyl]diphenyl-phosphine oxide. This material was dried under high vacuum, and was added 5 ml tetrahydrofuran; the solution was stirred and cooled to −70° C., and 0.78 ml (1.246 mmol) of 1.6 M BuLi in hexane was added. (The red color persisted after the initial 0.16 ml was added). The solution was stirred at −70° C. for 10 min, and then a solution of 0.2904 gr (0.796 mmol) of [1S-(1α, 3aβ,7aα] octahydro-7a-methyl-1-[1-[4-methyl-4-oxy]-2-pentanyl-cyclo-propyl]-4H-inden-4-one dissolved in 8 ml tetrahydrofuran was added dropwise. When the reaction was virtually complete (TLC, 1:9 ethyl acetate-hexane), the mixture was allowed to warm to −30° C., then 12 ml of pH 7 phosphate buffer (139.4 gr of dipotassium phosphate in 400 ml of water plus 10 ml of 2M phosphoric acid) was added dropwise through the center port. The mixture was stirred for 5 min, then transferred to a separatory funnel with the aid of 35 ml of hexane. The aqueous phase was re-extracted with 30 ml of hexane. The two hexane layer were combined, washed with 20 ml of brine, dried by passage through a plug of sodium sulfate, then evaporated to a colorless syrup. This material was taken in hexane. White solids were present so that hexane suspension had to be filtered through a flash column 25×120 mm. After fraction #2 (20 ml each) the mobile phase was changed to 1:79 ethylacetate-hexane. Fractions 11-18 (according to TLC in 1:19 ethyl acetate-hexane) were pooled and evaporated. It gave 0.4202 gr (88.1%) of silylated title compound.

A 100 ml brown round-bottom flask was charged with 0.4202 gr of silylated title compound. To this material was added 5 ml tetrahydrofuran and 3.5 ml of a 1 M solution of tetrabutylammonium fluoride in tetrahydrofuran and stirred at room temperature for 17 hrs. TLC (1:1 ethyl acetate-hexane and ethyl acetate) showed one major spot. The reaction mixture was then diluted with 13 ml of brine, stirred for 15 min, then transferred to a separatory funnel with aid of 40 ml ethyl acetate. The aqueous layer was re-extracted with 20 ml of ethyl acetate. Both organic layers were combined and washed with 5×35 ml water and once with brine, then passed through a plug of sodium sulfate and evaporated to a crystalline, white residue, 0.3523 gr. This material was chromatographed on a 25×10 mm column using 1:1 ethyl acetate-hexane as mobile phase. Fractions 3-4, already crystallizing in the tubes. The suspension so obtained was concentrated to a volume of ca 5 ml, diluted with hexane and concentrated, and filtered to give crystalline title compound 0.2567 gr. $[\alpha]_D^{25}$ −59.1° (c 0.325, EtOH). UV$\lambda_{max}$ (MeOH): 214, 262; $\lambda_{sh}$ 222 nm. Anal. Calcd for $C_{28}H_{44}O$: C, 81.50; H, 10.75; 0, 7.75. Found: C, 81.43; H, 10.69; 0, 7.48.

TABLE 1

Representative compounds of Formula I.

| Cpd. # | Structure |
|---|---|
| 24 | 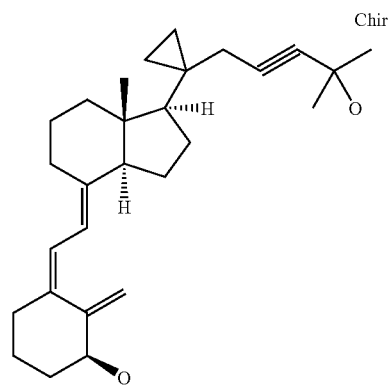 |
| 26 | 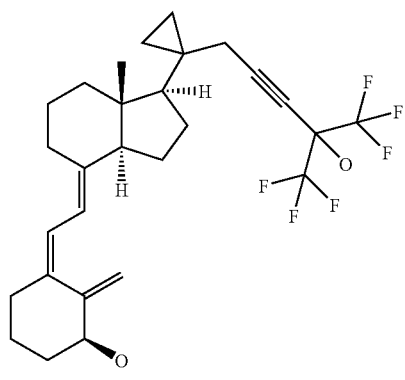 |
| 27 | 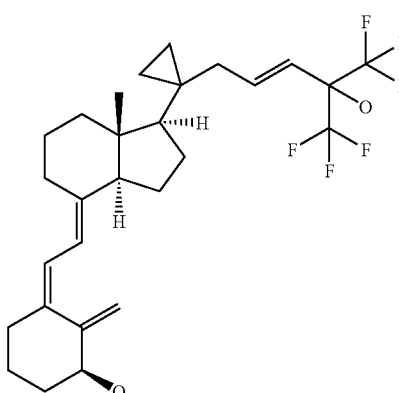 |

TABLE 1-continued

Representative compounds of Formula I.

| Cpd. # | Structure |
|---|---|
| 32 | 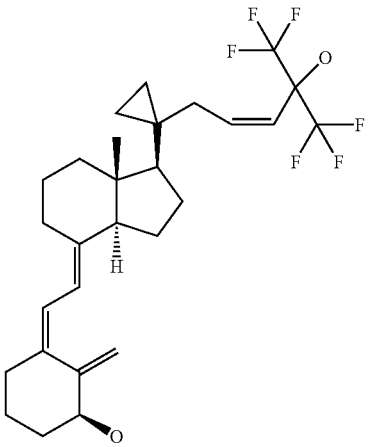 |
| 34 | 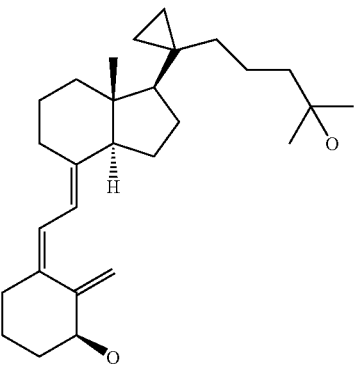 |

In the above Table, unshared valences on oxygen are intended to be occupied by hydrogen.

Example 9

This example illustrates comparative in vivo efficacy of Compound 7 and 1,25-(OH)$_2$ Vitamin D$_3$.

Comparison of the efficacy of Compound 7 to that of 1,25-dihydroxy vitamin D$_3$ (i.e., VD$_3$), was made using the standard animal model for post menopausal osteopenia, the rat ovariectomy model. Three month old rats weighing 285gm were ovariectomized (OVX), and then treated for 8 weeks beginning 1 week post OVX. Drugs were administered once/day orally in miglyol (medium chain triglyceride) vehicle. Blood and urine samples were collected at the 3 wk and 6 wk timepoint, and bone mineral density (BMD) was determined in vivo at 6 wk using Dual Energy X-ray Absorptiometry (Hologic QDR-4500™ Bone Scanner). At 8 weeks, the animals were sacrificed, and the lumbar vertebrae and femur bones removed for ex vivo BMD determination (Lunar Pixi-Mus™ Bone Scanner) and biomechanical testing for strength. Data for each compound are reported in the accompanying tables for the highest safe doses. The highest safe dose is defined as that which does not produce hypercalcemia as defined by serum calcium levels greater than 10.0 mg/dl.

Table 3 shows the safety (serum calcium, urinary calcium) results. The doses being compared all gave 3 wk serum calcium levels of 9.3 mg/dl, and 6 wk levels of 9.8±0.1 mg/dl. At these doses, the urinary calcium output per 24 hr sample was the same for the 0.4 nmol/kg dose of VD$_3$ and the 0.5 nmol/kg dose of Compound 7. Table 4 shows the efficacy parameters for the 2 compounds (BMD, biomechanics, and urinary deoxypyridinolines). BMD at all of the bone sites listed is significantly higher in the animals dosed with Compound 7 than those dosed with VD3 at doses which give equivalent serum calcium levels. These doses represent those expected to give maximal efficacy achievable safely, as higher doses of each compound are known to be hypercalcemic. Urinary deoxy-pyridinolines, a marker of bone resorption were significantly less for Compound 7 than VD$_3$ at 6 weeks showing greater ability of Compound 7 to inhibit bone resorption. Compound 7 treatment resulted in stronger vertebral bone. Failure Load, the amount of force needed to fracture the L5 vertebra, was determined in axial compression testing. Significantly more force was needed to fracture the vertebrae of animals treated with Compound 7 compared to those treated with VD$_3$ at the highest safe doses.

TABLE 3

Safety Comparison of Compound 7 to 1,25-dihydroxy-Vitamin D$_3$ (VitD)

| PARAMETER | | | SHAM Control | OVX Control | VitD 0.012 nmol/kg p vx controls | VitD 0.04 nmol/kg p vs controls | Compound 27 0.5 nmol/kg p vs controls | p vs 0.012 VD3 | p vs 0.04 VD3 |
|---|---|---|---|---|---|---|---|---|---|
| SERUM & URINE CALCIUM | | | | | | | | | |
| SERUM CALCIUM (mg/dl) | Week 3 | Mean | 9.4 | 9.2 | 9.3 nd | 9.3 ns | 9.3 ns | ns | ns |
| | | SEM | 0.1 | 0.1 | 0.1 | 0.1 | 0.1 | | |
| | | n/group | 10 | 10 | 10 | 10 | 10 | | |
| | Week 6 | Mean | 9.5 | 9.3 | 9.8 **+ | 9.7 ** | 9.9 **+ | ns | ns |
| | | SEM | 0.1 | 0.1 | 0.1 | 0.1 | 0.2 | | |
| | | n/group | 10 | 10 | 10 | 9 | 10 | | |
| URINARY CALCIUM (MG/MMOL Creatineine/day) | Week 3 | Mean | 0.31 | 0.22 | 0.31 ** | 0.51 **+ | 0.51 **+ | $ | ns |
| | | SEM | 0.02 | 0.05 | 0.04 | 0.05 | 0.06 | | |
| | | n/group | 10 | 10 | 10 | 10 | 10 | | |

TABLE 3-continued

Safety Comparison of Compound 7 to 1,25-dihydroxy-Vitamin $D_3$ (VitD)

| PARAMETER | | | SHAM Control | OVX Control | VitD 0.012 nmol/kg p vs controls | VitD 0.04 nmol/kg p vs controls | Compound 27 0.5 nmol/kg p vs controls | p vs 0.012 VD3 | p vs 0.04 VD3 |
|---|---|---|---|---|---|---|---|---|---|
| | Week 6 | Mean | 0.34 | 0.26 | 0.43 ** | 0.71 **++ | 0.72 **++ | $ | ns |
| | | SEM | 0.03 | 0.05 | 0.04 | 0.05 | 0.07 | | |
| | | n/group | 10 | 10 | 10 | 9 | 10 | | |

ND = no data available
ns = not significantly different
*$p < 0.05$, **$p < 0.01$ vs OVX Control
+$p < 0.05$, ++$p < 0.01$ vs OVX Control
$$p < 0.05$, $$$$p < 0.01$ vs Vit-D

TABLE 4

Efficacy Comparison of Compound 7 to 1,25-dihydroxy-Vitamin $D_3$ (VitD)

| PARAMETER | | | SHAM COntrol | OVX Control | VitD 0.012 nmol/kg | VitD 0.04 nmol/kg | Compound 27 0.5 nmol/kg | p vs 0.012 VD3 | p vs 0.04 VD3 |
|---|---|---|---|---|---|---|---|---|---|
| PERCENT BMD > OVX CONTROL in vivo | | | | | | | | | |
| L2-L4 Vertebrae | Week 6 | Mean | 10.0 | 0.0 | 3.3 ++ | 5.4 * | 10.3 ** | $$ | S |
| | | S.E.M. | 1.9 | 1.6 | 1.6 | 1.6 | 2.1 | | |
| | | n/group | 9 | 9 | 10 | 9 | 10 | | |
| L5 vertebrae | Week 6 | Mean | 11.6 | 0.0 | 2.7 ++ | 4.9 ++ | 8.7 ** | $ | ns |
| | | S.E.M. | 1.2 | 1.2 | 2.3 | 1.4 | 2.0 | | |
| | | n/group | 9 | 9 | 10 | 9 | 10 | | |
| Whole Femur | Week 6 | Mean | 7.3 | 0.0 | 3.3 + | 1.9 ++ | 6.3 ** | ns | $ |
| | | S.E.M. | 1.1 | 0.8 | 1.7 | 1.7 | 1.1 | | |
| | | n/group | 9 | 9 | 10 | 9 | 10 | | |
| Prox Femur | Week 6 | Mean | 6.5 | 0.0 | 3.5 ns | 0.7 ++ | 5.7 ** | ns | $$ |
| | | S.E.M. | 1.5 | 1.4 | 1.7 | 1.5 | 1.2 | | |
| | | n/group | 9 | 9 | 10 | 9 | 10 | | |
| Distal Femur | Week 6 | Mean | 11.7 | 0.0 | 2.8 ++ | 2.8 ++ | 8.5 ** | $$ | $$ |
| | | S.E.M. | 1.2 | 1.1 | 1.8 | 2.0 | 1.3 | | |
| | | n/group | 9 | 9 | 10 | 9 | 10 | | |
| L5 Bone Density Ex Vivo | | | | | | | | | |
| BMD (g/cm^2) | Week 8 | Mean | 0.113 | 0.098 | 0.103 ++ | ND | 0.112 ** | $$ | ND |
| | | S.E.M. | 0.002 | 0.002 | 0.003 | | 0.002 | | |
| | | n/group | 10 | 7 | 9 | | 10 | | |
| BMC (g) | Week 8 | Mean | 0.038 | 0.033 | 0.035 ns | ND | 0.039 ** | $$ | ND |
| | | S.E.M. | 0.001 | 0.001 | 0.002 | | 0.001 | | |
| | | n/group | 10 | 7 | 9 | | 10 | | |
| URINARY D-PYD | | | | | | | | | |
| (nM/mM Creatinine) | Week 3 | Mean | 0.38 | 0.90 | 0.81 ++ | 0.75 ++ | 0.65 *+ | ns | ns |
| | | S.E.M. | 0.04 | 0.06 | 0.09 | 0.07 | 0.09 | | |
| | | n/group | 10 | 10 | 9 | 9 | 10 | | |
| | Week 6 | Mean | 0.31 | 0.84 | 0.78 ++ | 0.76 ++ | 0.57 **+ | $ | $ |
| | | S.E.M. | 0.03 | 0.07 | 0.09 | 0.09 | 0.06 | | |
| | | n/group | 10 | 10 | 10 | 8 | 10 | | |
| L5 Vertebral Body BIOMECHANICS | | | | | | | | | |
| Failure Load (N) | Week 8 | Mean | 386 | 261 | 342 * | ND | 419 ** | $ | ND |
| | | S.E.M. | 32 | 20 | 26 | | 23 | | |
| | | n/group | 7 | 6 | 9 | | 10 | | |

ND = no data available
ns = not significantly different
*$p < 0.05$, **$p < 0.01$ vs OVX Control
+$p < 0.05$, ++$p < 0.01$ vs OVX Control
$$p < 0.05$, $$$$p < 0.01$ vs Vit-D

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A method for treating osteoporosis or hyperparathyroidism in a patient comprising administering a 3-desoxy vitamin $D_3$ analog to the patient, wherein said 3-desoxy vitamin $D_3$ analog is of the formula:

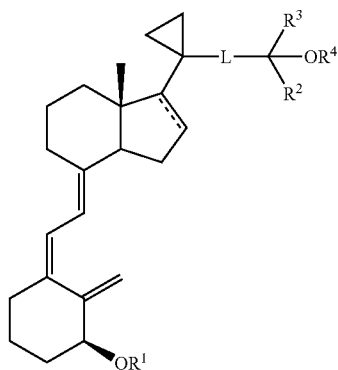

or a salt thereof,
wherein
dotted line is optionally a double bond;
L is a linker selected from the group consisting of:

—$CH_2$—$CH_2$—$CH_2$—,

—$CH_2$—CH=CH—,

—$CH_2$—C≡C—,

—$CH_2$—$CH_2$—C(=O)—, and

—CH=CH—CH=CH—;

each of $R^1$ and $R^4$ is selected from the group consisting of hydrogen or alkyl; and
each of $R^2$ and $R^3$ is independently selected from the group consisting of alkyl or haloalkyl, or $R^2$ and $R^3$ and together with the carbon atom to which they are attached to form a cycloalkyl.

2. The method of claim 1, wherein said 3-desoxy vitamin $D_3$ analog is of the formula:

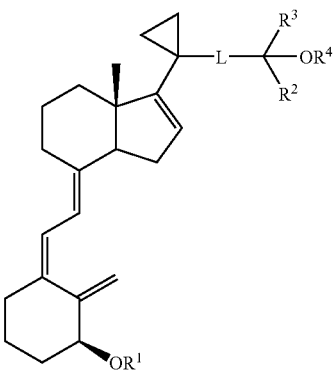

wherein $R^1$, $R^2$, $R^3$, $R^4$ and L are those defined in claim 1.

3. The method of claim 2, wherein said linker L is selected from the group consisting of:

—$CH_2$—$CH_2$—$CH_2$—;

—$CH_2$—CH=CH—;

—$CH_2$—C≡C—; and

—CH=CH—CH=CH—.

4. The method of claim 3, wherein said linker L is selected from the group consisting of:

—$CH_2$—CH=CH—; and

—$CH_2$C≡C—.

5. The method of claim 4, wherein $R^1$ is hydrogen.

6. The method of claim 4, wherein $R^1$ and $R^4$ are hydrogen.

7. The method of claim 4, wherein each of $R^2$ and $R^3$ is independently selected from the group consisting of alkyl and haloalkyl.

8. The method of claim 7 wherein $R^2$ and $R^3$ are both trifluoromethyl.

9. The method of claim 1, wherein the disease is osteoporosis.

10. The method of claim 1, wherein the patient is also treated with a bisphosphonate, estrogen, selective estrogen receptor modulator or anabolic agent.

* * * * *